United States Patent
Yerby

(10) Patent No.: US 8,143,596 B2
(45) Date of Patent: Mar. 27, 2012

(54) ULTRAVIOLET STERILIZATION CHAMBER WITH HOOKS FOR ATTACHING OBJECTS TO BE STERILIZED

(76) Inventor: Earl Yerby, Apex, NC (US)

( * ) Notice: Subject to any disclaimer, the term of this patent is extended or adjusted under 35 U.S.C. 154(b) by 223 days.

(21) Appl. No.: 12/512,766

(22) Filed: Jul. 30, 2009

(65) Prior Publication Data

US 2010/0314553 A1    Dec. 16, 2010

Related U.S. Application Data

(60) Provisional application No. 61/268,365, filed on Jun. 11, 2009.

(51) Int. Cl.
*G01N 23/00* (2006.01)
(52) U.S. Cl. .................................. 250/455.11
(58) Field of Classification Search ............. 250/455.11; 362/396
See application file for complete search history.

(56) References Cited

U.S. PATENT DOCUMENTS

| | | | | |
|---|---|---|---|---|
| 4,128,226 A * | 12/1978 | Ross et al. | ..................... | 362/378 |
| 4,321,232 A | 3/1982 | Bithell | | |
| 4,505,545 A * | 3/1985 | Salia-Munoz | ................ | 359/896 |
| 4,917,586 A * | 4/1990 | Jacob | .............................. | 422/21 |
| 5,163,751 A * | 11/1992 | Bottiglieri | ..................... | 362/376 |
| 5,225,160 A | 7/1993 | Sanford | | |
| 5,342,582 A | 8/1994 | Horn | | |
| 5,597,597 A * | 1/1997 | Newman | ....................... | 426/248 |
| 5,730,934 A | 3/1998 | Holbert | | |
| 5,786,598 A | 7/1998 | Clark | | |
| 5,836,669 A * | 11/1998 | Hed | ................................. | 362/92 |
| 5,843,374 A | 12/1998 | Sizer | | |
| 5,879,620 A | 3/1999 | Cohen | | |
| 5,993,739 A | 11/1999 | Lyon | | |
| 6,605,260 B1 | 8/2003 | Busted | | |
| 6,749,806 B2 | 6/2004 | Koji | | |
| 6,814,932 B2 | 11/2004 | Hlebovy | | |
| 6,923,367 B1 * | 8/2005 | Grossman et al. | .............. | 232/17 |
| 7,038,219 B2 | 5/2006 | Clark | | |
| 7,160,566 B2 * | 1/2007 | Fink et al. | ..................... | 426/235 |
| 7,511,283 B2 * | 3/2009 | Chor | ........................ | 250/455.11 |
| 7,560,706 B1 * | 7/2009 | Castelluccio | ............ | 250/455.11 |
| 7,791,044 B1 * | 9/2010 | Taylor et al. | ............ | 250/455.11 |
| 2005/0230639 A1 * | 10/2005 | Ancona et al. | ........... | 250/455.11 |
| 2005/0274906 A1 * | 12/2005 | Riddell | ..................... | 250/455.11 |
| 2009/0065716 A1 * | 3/2009 | Ullman | ..................... | 250/504 R |
| 2009/0148358 A1 * | 6/2009 | Wind | .......................... | 422/186.3 |
| 2010/0044582 A1 * | 2/2010 | Cooper et al. | ........... | 250/455.11 |
| 2010/0148090 A1 * | 6/2010 | Chang | ..................... | 250/455.11 |

* cited by examiner

*Primary Examiner* — Jack Berman
*Assistant Examiner* — Jason McCormack
(74) *Attorney, Agent, or Firm* — Moore & Van Allen PLLC

(57) ABSTRACT

An article sanitizer includes a rigid opaque enclosure open at a door side thereof. An enclosure door is adapted to selectively close the door side of the enclosure. At least one UV bulb is fixed to at least one bulb fixture within the enclosure and extends at least partially into the open internal space of the enclosure. A cage is fixed around each sanitizer bulb. An article fastener is fixed with the cage and is adapted to be selectively fastened to the article for securing the article thereto. An electronic circuit is electrically connected to each sanitizer bulb and is adapted to power each bulb for a present period of time. A switch may be included proximate the door and adapted to electrically close when the door is closed to prevent bulb activation when the door is open. A wheeled support stand may be fixed with the enclosure.

12 Claims, 2 Drawing Sheets

ULTRAVIOLET STERILIZATION CHAMBER WITH HOOKS FOR ATTACHING OBJECTS TO BE STERILIZED

CROSS-REFERENCE TO RELATED APPLICATIONS

This application claims the benefit of U.S. Provisional Patent Application 61/268,365, filed on Jun. 11, 2009, and incorporated herein by reference.

STATEMENT REGARDING FEDERALLY SPONSORED RESEARCH AND DEVELOPMENT

Not Applicable.

FIELD OF THE INVENTION

This invention relates to sanitizing, and more particularly to a sanitizer for articles that utilizes ultraviolet light.

DISCUSSION OF RELATED ART

Sports bags, reusable grocery bags, sporting equipment such as cleats, helmets, and similar objects that come into contact with unsanitary objects often themselves become unsanitary as a result of such contact. Over time, such articles that are not sanitized can promote the growth of bacteria, mold and fungus, and result in further spread of disease.

Sanitizing devices are known in the art. For example, U.S. Pat. No. 6,923,367 to Grossman et al. on Aug. 2, 2005, teaches a mailbox enclosure for sanitizing mail articles with UV light and other means. Such a device is not well suited, however, for other types of articles, particularly articles having an interior space such as reusable grocery bags, sporting helmets, and the like. Further, such a device is not easily moved from one location to another.

U.S. Pat. No. 6,605,260 to Busted on Aug. 12, 2003, teaches a surgical tool sterilizing enclosure that utilizes UV light as well as chemical and other sanitizing agents. Such a device is also not well-suited for the sanitation of articles having an interior space, but rather for articles having an outer surface that needs decontamination. Such a device is also not well-suited for portable use.

Therefore, there is a need for a device that substantially sanitizes an article, and particularly an article having an interior space such as a reusable grocery bag, sporting equipment such as helmets, shoes, or the like. Such a needed device would be extremely simple to use, and relatively inexpensive to manufacture and operate. The needed invention would be easily moved from location to location as needed, such as within a grocery store, for example. The present invention accomplishes these objectives.

SUMMARY OF THE INVENTION

The present device is a sanitizer for an article, such as a bag having at least one handle, or athletic equipment (not shown) such as shoes, helmets, or the like. A rigid opaque enclosure is open at a door side and includes at least one bulb attachment means fixed internally thereto. The enclosure includes an open internal space therein. An enclosure door, preferably hinged to the enclosure, is adapted to selectively close the door side of the enclosure, substantially sealing the open space therein and substantially preventing light from escaping from the internal space.

At least one sanitizer bulb, such as a UV fluorescent bulb, is fixed to the bulb attachment means and extends at least partially into the open internal space of the enclosure. A rigid, at least partially non-opaque cage is fixed around each sanitizer bulb. An article fastening means is fixed to the cage and is adapted to be selectively fastened to the article for securing the article to the cage. In the embodiment wherein the article is the bag having handles, the bag fastening means may be a pair of handle hooks, for example.

An electronic circuit means is electrically connected to each sanitizer bulb and is adapted to power each bulb for a present period of time. A switch is preferably included proximate the door and adapted to electrically close when the door is closed, such that each sanitizer bulb cannot be illuminated unless the door is closed and the switch is closed. The electronic circuit means may include a mechanically or electronically-driven timer means for timing the duration of sanitizer bulb activation.

A support stand may be fixed with the enclosure and adapted for holding the enclosure above a ground surface. Such a support stand may further include a pair of wheels at a lower end thereof, such that the enclosure and support stand may be tilted backward until each wheel engages the ground surface for rolling the sanitizer therealong.

The present invention is a device that substantially sanitizes an article, and particularly an article having an interior space such as a reusable grocery bag, sporting equipment such as helmets, shoes, or the like. The present device is extremely simple to use, and relatively inexpensive to manufacture and operate. The present invention may be easily moved from location to location as needed, such as within a grocery store, for example. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. Any use of the word "means" herein is intended to invoke means-plus-function limitation in accordance with 35 U.S.C. §112, sixth paragraph, even if the word "means" follows words describing the function.

Figure 1:
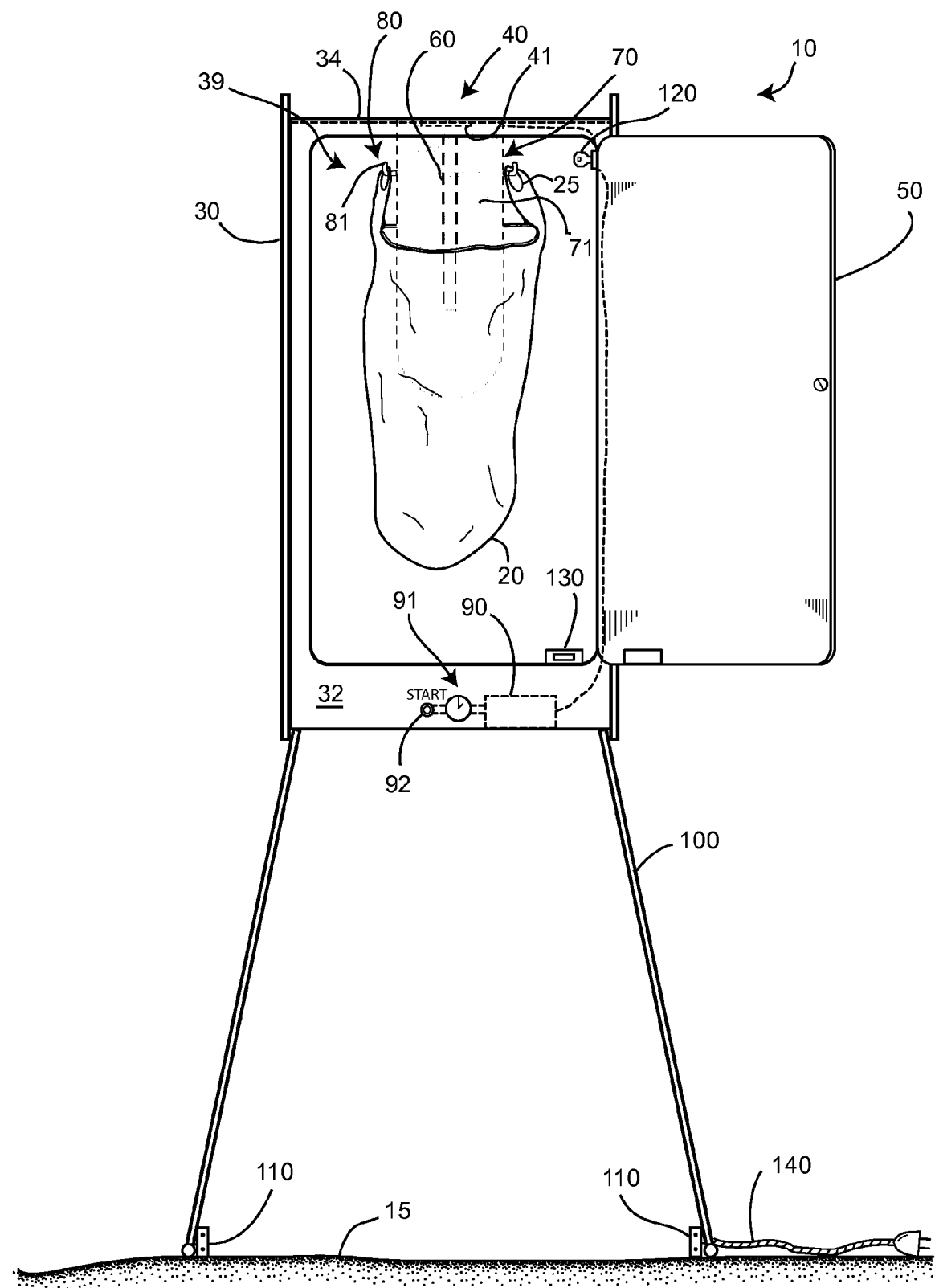
FIG. 1 is a right-side elevational view of the invention, partially cut-away to show an internal space within an enclosure thereof.
Figure 2:
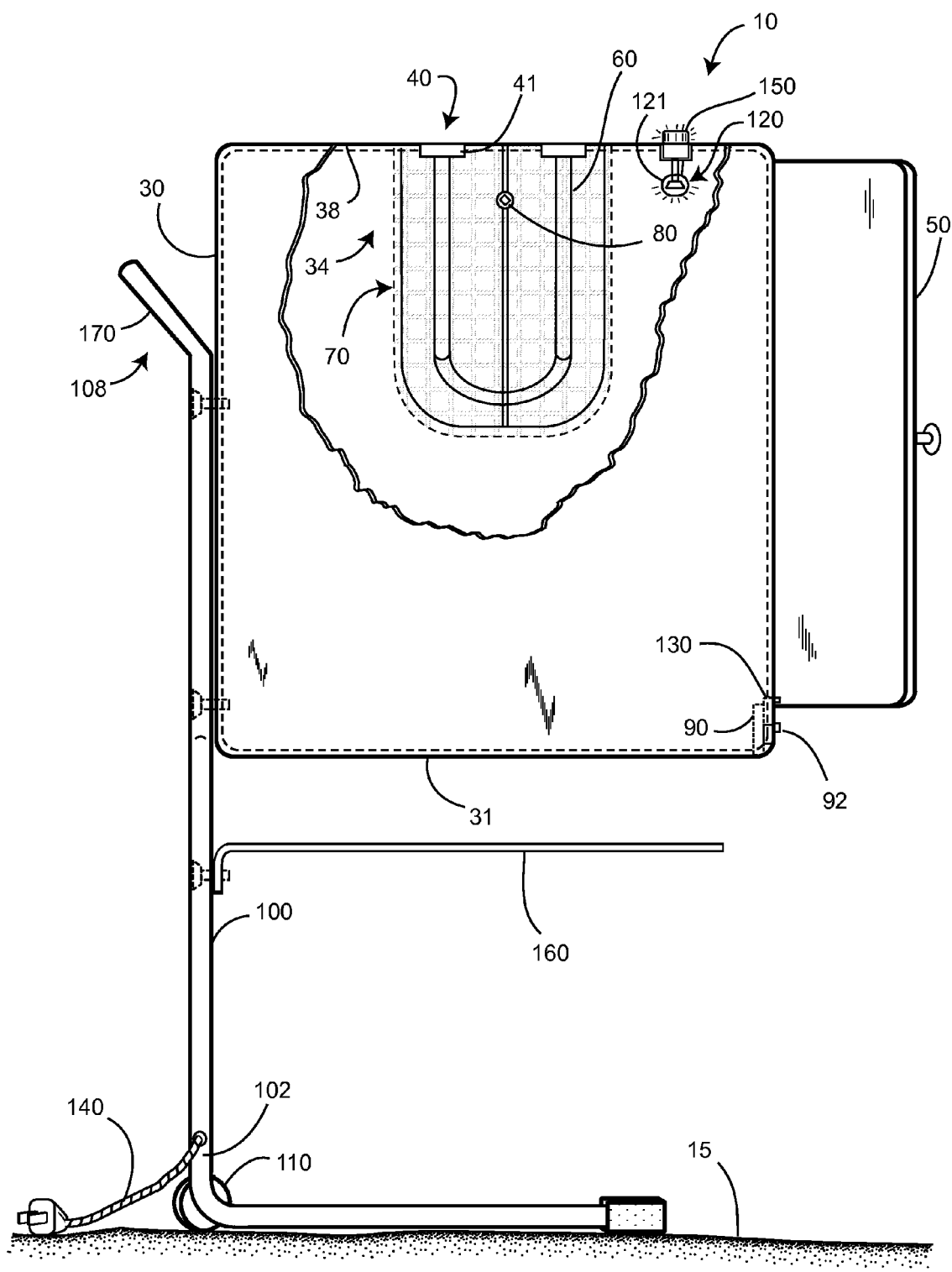
FIG. 2 is a front elevational view thereof, illustrating an article as attached to a bulb-protective cage thereof.

FIGS. 1 and 2 illustrate a sanitizer 10 for an article 20, such as a bag 20 having at least one handle 25, or athletic equipment (not shown) such as shoes, helmets, or the like. A rigid opaque enclosure 30 is open at a door side 32 and includes at least one bulb attachment means 40, such as a fluorescent bulb socket 41, an incandescent lamp socket (not shown), or the like, fixed internally thereto at one end 34 thereof, such as a top end 38. The enclosure 30 includes an open internal space 39 therein, and is preferably made from an opaque acrylic material, or the like. As such, each side of the enclosure 30 may be adhered with a methylene chloride and diacetone alcohol adhesive, for example. Sides of the enclosure may include advertising support means (not shown), such as J-shaped channels, so that advertising or other printed materials may be displayed on the sides of the enclosure 30.

An enclosure door 50, preferably hinged to the enclosure, is adapted to selectively close the door side 32 of the enclosure 30, substantially sealing the open space 39 therein and substantially preventing light from escaping from the internal space 39. Optionally, interior surfaces of the enclosure 30 may be coated with an ultraviolet light-reflective coating, such as a mirror, reflective paint, or the like. A spring (not shown) may be included for urging the door 50 into its closed position unless pulled open.

At least one sanitizer bulb 60, such as a UV fluorescent bulb, is fixed to the bulb attachment means 40 and extends at least partially into the open internal space 39 of the enclosure 30. A rigid, at least partially non-opaque cage 70 is fixed around each sanitizer bulb 60. Such a cage 70 may be made from a metallic mesh 71, or a non-opaque plastic material (not shown), or the like, or a combination thereof.

An article fastening means 80 is fixed to the cage 70 and is adapted to be selectively fastened to the article 20 for securing the article 20 to the cage 70. In the embodiment wherein the article 20 is the bag 20 having handles 25, the bag fastening means 80 may be a pair of handle hooks 81, for example. Other embodiments designed for alternate articles 20 may be used, such as wherein the articles 20 are shoes, helmets, or other sporting equipment, or the like (not shown). In such an embodiment the article fastening means 80 may be spring clips (not shown), hooks, clamps, or the like. In one embodiment, the one end 34 of the enclosure 30 is a bottom end 31, such that each sanitizer bulb 60 extends upwardly from the bottom end 34 of the enclosure 30 and the articles is supported on the cage 70 by gravity (not shown). In such an embodiment, the bag 20 may be inverted and secured around the cage 70 and held thereon by gravity.

An electronic circuit means 90 is electrically connected to each sanitizer bulb 60 and is adapted to power each bulb 60 for a present period of time. A switch 130 is preferably included proximate the door 50 and adapted to electrically close when the door 50 is closed, such that each sanitizer bulb 60 cannot be illuminated unless the door 50 is closed and the switch 130 is closed. The electronic circuit means 90 may include a mechanically or electronically-driven timer 91 for timing the duration of sanitizer bulb 60 activation. A start button 92 may be included as an interface between a user and the electronic circuit means 90, the start button 92 when depressed activating each sanitizer bulb 60 and initiating the timer 91.

A support stand 100 may be fixed with the bottom end 31 of the enclosure 30 and adapted for holding the enclosure 30 above a ground surface 15 for convenient loading and unloading of the article 20. Such a support stand 100 may further include a pair of wheels 110 at a lower end 102 thereof, such that the enclosure 30 and support stand 100 may be tilted backward until each wheel 110 engages the ground surface 15 for rolling the sanitizer 10 therealong. A power cord 140 may be fixed with the stand 100 and electrically connected to the electronic circuit means 90. Article supports 160 may be fixed with the support stand 100 for storing and dispensing a plurality of the articles 20.

Preferably the stand 100 is made from 1"×2" aluminum tubing, all joints being welded (not shown). The stand 100 may be wider at the bottom end 102 thereof for additional stability of the stand 100. Each wheel 110 may be a 4" diameter coaster, for example. The stand 100 may further include a handle 170 at a top end 108 thereof, such that the stand 100 and enclosure 30 may be tilted back on the wheels 110 while gripping the handle 170, such as with a conventional hand truck.

Further, a non-UV light bulb 120, such as an incandescent bulb 121 or at least one white-colored LED (not shown), may be included within the enclosure 30 for illuminating the internal space 39 thereof when the switch 130 detects that the door 50 is not closed. Such a non-UV light bulb 120 is preferably electrically connected to the electronic circuit means 90.

As such, with the article fixed to or around the cage 70, and with the door 50 closed and the electronic circuit 90 activated, such as by the user pressing the "start" button 92, each sanitizer bulb 60 is illuminated for the preset period of time to sanitize the article 20. After the preset time has elapsed, each sanitizer bulb 60 is deactivated and, optionally, an indicator 150, such as an LED lamp or the like, is activated to indicate that the article 20 is substantially sanitized. Upon opening of the door 50, the non-UV bulb 120 is activated and the indicator 150 is deactivated.

While a particular form of the invention has been illustrated and described, it will be apparent that various modifications can be made without departing from the spirit and scope of the invention. For example, the specific type of cage 70 and article fastening means 80 may vary according to the type of article 20 to be sanitized. Accordingly, it is not intended that the invention be limited, except as by the appended claims.

The teachings provided herein can be applied to other systems, not necessarily the system described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the system may vary considerably in its implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A sanitizer for a bag having at least one handle, comprising:
    a rigid opaque enclosure open at a door side and including at least one fluorescent bulb socket fixed internally thereto at one end thereof, the enclosure including an open internal space therein;
    an enclosure door adapted to selectively close the door side of the enclosure, substantially sealing the open space therein;
    at least one fluorescent UV sanitizer bulb fixed to the fluorescent bulb socket and extending at least partially into the open internal space of the enclosure;
    a rigid, at least partially non-opaque metallic mesh cage fixed around each sanitizer bulb;
    a pair of handle hooks fixed to the cage and each adapted to be selectively fastened to one handle of the bag for securing the bag around the cage;
    an electronic circuit electrically connected to each sanitizer bulb and adapted to power each bulb for a preset period of time, the electronic circuit including a switch proximate the door and adapted to close when the door is closed, such that each sanitizer bulb cannot be illuminated unless the door is closed;
    a support stand fixed to a bottom end of the enclosure, the support stand adapted for holding the enclosure above a ground surface for loading and unloading of the bag, the support stand including a pair of wheels at a lower end thereof, such that the enclosure and support stand may be tilted backward until each wheel engages the ground surface for rolling the sanitizer therealong;
    a non-UV light bulb for illuminating the internal space of the enclosure when the switch detects that the door is not closed, the non-UV light bulb electrically connected to the electronic circuit;
    whereby with the bag fixed around the cage and to the handle hooks, and with the door closed and the electronic circuit activated, each sanitizer bulb is illuminated for the present preset period of time to sanitize the inside of the bag.

2. The sanitizer of claim 1 wherein the one end of the enclosure is a bottom end, such that each sanitizer bulb extends upwardly from the bottom end of the enclosure.

3. The sanitizer of claim 1 wherein the electronic circuit includes a mechanically-driven timer.

4. The sanitizer of claim 1 wherein the non-UV light bulb is an incandescent bulb.

5. The sanitizer of claim 1 wherein the non-UV light bulb is at least one white-colored LED.

6. The sanitizer of claim 1 wherein the electronic circuit includes an electronically-driven timer.

7. A sanitizer for a bag having at least one handle, comprising:
    a rigid opaque enclosure open at a door side and including at least one fluorescent bulb socket fixed internally thereto at one end thereof, the enclosure including an open internal space therein;
    an enclosure door adapted to selectively close the door side of the enclosure, substantially sealing the open space therein;
    at least one fluorescent UV sanitizer bulb fixed to the fluorescent bulb socket and extending at least partially into the open internal space of the enclosure;
    a rigid, non-opaque plastic cage fixed around each sanitizer bulb;
    a pair of handle hooks fixed to the cage and each adapted to be selectively fastened to one handle of the bag for securing the bag around the cage;
    an electronic circuit electrically connected to each sanitizer bulb and adapted to power each bulb for a preset period of time, the electronic circuit including a switch proximate the door and adapted to close when the door is closed, such that each sanitizer bulb cannot be illuminated unless the door is closed;
    a support stand fixed to a bottom end of the enclosure, the support stand adapted for holding the enclosure above a ground surface for loading and unloading of the bag, the support stand including a pair of wheels at a lower end thereof, such that the enclosure and support stand may be tilted backward until each wheel engages the ground surface for rolling the sanitizer therealong;

a non-UV light bulb for illuminating the internal space of the enclosure when the switch detects that the door is not closed, the non-UV light bulb electrically connected to the electronic circuit;

whereby with the bag fixed around the cage and to the handle hooks, and with the door closed and the electronic circuit activated, each sanitizer bulb is illuminated for the preset period of time to sanitize the inside of the bag.

8. The sanitizer of claim 7 wherein the one end of the enclosure is a bottom end, such that each sanitizer bulb extends upwardly from the bottom end of the enclosure.

9. The sanitizer of claim 7 wherein the electronic circuit includes a mechanically-driven timer.

10. The sanitizer of claim 7 wherein the electronic circuit includes an electronically-driven timer.

11. The sanitizer of claim 7 wherein the non-UV light bulb is an incandescent bulb.

12. The sanitizer of claim 7 wherein the non-UV light bulb is at least one white-colored LED.

* * * * *

UNITED STATES PATENT AND TRADEMARK OFFICE
CERTIFICATE OF CORRECTION

| | | |
|---|---|---|
| PATENT NO. | : 8,143,596 B2 | Page 1 of 1 |
| APPLICATION NO. | : 12/512766 | |
| DATED | : March 27, 2012 | |
| INVENTOR(S) | : Earl Yerby | |

It is certified that error appears in the above-identified patent and that said Letters Patent is hereby corrected as shown below:

IN THE CLAIMS:

In column 6, Claim 1, please change line 29 to:

"for the preset period of time to sanitize the inside"

Signed and Sealed this
Tenth Day of July, 2012

David J. Kappos
*Director of the United States Patent and Trademark Office*